United States Patent
Morales Ramos et al.

(10) Patent No.: US 11,051,490 B2
(45) Date of Patent: Jul. 6, 2021

(54) INSECT WATER SUPPLY SYSTEM

(71) Applicant: The United States of America, as represented by the Secretary of Agriculture, Washington, DC (US)

(72) Inventors: Juan A. Morales Ramos, Greenville, MS (US); Scott L. Lee, Cleveland, MS (US); Maria G. Rojas, Greenville, MS (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 548 days.

(21) Appl. No.: 15/935,403

(22) Filed: Mar. 26, 2018

(65) Prior Publication Data

US 2018/0271056 A1 Sep. 27, 2018

Related U.S. Application Data

(60) Provisional application No. 62/477,098, filed on Mar. 27, 2017.

(51) Int. Cl.
*A01K 67/033* (2006.01)
*A01K 7/00* (2006.01)

(52) U.S. Cl.
CPC .............. *A01K 7/00* (2013.01); *A01K 67/033* (2013.01); *A01K 2227/706* (2013.01)

(58) Field of Classification Search
CPC . A01K 7/00; A01K 7/02; A01K 7/025; A01K 1/0356; A01K 39/00; A01K 39/02; A01K 39/0206; A01K 39/04; A01K 39/005; A01K 31/17; A01K 31/18; A01K 31/22; A01K 2227/706; A01K 67/00; A01K 67/033; A01K 67/0333; A01K 53/00; A23K 50/90; A01M 1/02; A01M 1/023; A01M 2200/01; A01M 2200/011; A01M 2200/012

See application file for complete search history.

(56) References Cited

U.S. PATENT DOCUMENTS

| | | | | | |
|---|---|---|---|---|---|
| 69,428 | A | * | 10/1867 | Harrison | ................ A01K 53/00 449/10 |
| 1,116,923 | A | * | 11/1914 | Rahn | ...................... A01K 47/06 449/10 |
| 1,414,284 | A | * | 4/1922 | Jones | ...................... A01K 53/00 449/9 |
| 3,345,974 | A | * | 10/1967 | Phillips | ................ A01K 67/033 119/51.01 |

(Continued)

FOREIGN PATENT DOCUMENTS

| WO | WO-9208356 A1 | * | 5/1992 | .............. A01M 1/02 |
| WO | WO-2010079353 A1 | * | 7/2010 | .......... A01M 1/2016 |
| WO | WO-2016015043 A1 | * | 1/2016 | ............. A01N 59/14 |

*Primary Examiner* — Kathleen I Alker
(74) *Attorney, Agent, or Firm* — John D. Fado; Robert D. Jones

(57) ABSTRACT

The insect water supply system is configured to prevent the insects (such as crickets) from self-contaminating the water supplied to the insects' rearing enclosure. The system is designed so that the insects drink in an inverted (i.e. upside down) and elevated position—consequently the insects' feces fall downward toward the ground and away from their water source—and therefore do not contaminate the insects' water supply.

15 Claims, 2 Drawing Sheets

(56) References Cited

U.S. PATENT DOCUMENTS

| | | | | |
|---|---|---|---|---|
| 4,250,581 | A * | 2/1981 | Kindall | A01K 53/00 449/9 |
| 4,322,862 | A * | 4/1982 | Beuthling | A01K 53/00 449/48 |
| 4,443,904 | A * | 4/1984 | van Muyden | A01K 47/00 449/6 |
| 4,765,275 | A * | 8/1988 | Yukawa | A01N 63/00 119/6.7 |
| 5,606,933 | A * | 3/1997 | Wilkins | A01K 39/0106 119/51.03 |
| 5,699,752 | A * | 12/1997 | Wilkins | A01K 39/0106 119/51.03 |
| 5,927,230 | A * | 7/1999 | Frank | G01N 1/24 119/6.5 |
| 7,229,627 | B2 * | 6/2007 | Hoffman | A01K 67/033 424/272.1 |
| 7,555,866 | B2 * | 7/2009 | Kania | A01G 9/00 47/59 R |
| 8,677,935 | B1 * | 3/2014 | Ilan | A01K 67/033 119/6.7 |
| 8,893,660 | B1 * | 11/2014 | Al-Azemi | A01K 53/00 119/72 |
| 9,173,389 | B2 * | 11/2015 | Boyd | A01M 29/12 |
| 10,051,845 | B1 * | 8/2018 | Massaro | A01K 29/005 |
| 10,779,526 | B1 * | 9/2020 | Aaron | A01M 1/103 |
| 2008/0173246 | A1 * | 7/2008 | Barkdoll | A01K 7/00 119/74 |
| 2014/0048017 | A1 * | 2/2014 | Mainini | A01K 5/00 119/51.01 |
| 2018/0007875 | A1 * | 1/2018 | Hall | A01K 7/02 |

* cited by examiner

INSECT WATER SUPPLY SYSTEM

REFERENCE TO RELATED APPLICATIONS

This application claims the benefit of U.S. Provisional Application No. 62/477,098, filed Mar. 27, 2017, which is incorporated herein by reference in its entirety.

FIELD OF THE INVENTION

The disclosed method and apparatus relates to supplying crickets (or other insects in culture) with water. Specifically, the method and apparatus described herein relates to an inverted water system wherein water (or other selected liquids) migrates through a water-retaining porous and permeable material at a controlled rate so that water is continuously available to a selected insect population.

BACKGROUND OF THE INVENTION

The United Nations expects the human population to grow to over 9 billion by 2050. Humans consume 40% of the biomass that land and coastal seas produce. Approximately 70% of agricultural land, which represents 30% of all the land on earth, is used to raise livestock. Meanwhile, food reserves are at a 50 year low, yet demand for food is expected to increase 50% by 2030. About 178 million children around the world are stunted from malnutrition. Expanding land use for livestock production as a source of animal protein is neither feasible nor sustainable.

Insects, such as crickets, represent an alternative source of animal protein. Insects can be farmed using less land, feed, water, and other resources than conventional livestock, and crickets convert/metabolize food more efficiently. For instance, house crickets (*Acheta domesticus* (L.)) have twice the efficiency of conversion of ingested food than pigs and chickens, 4 times that of sheep, and 6 times that of cattle. To produce 1 kilogram weight of crickets, the amount of feed required is 1.7 kilograms, less than 1 liter of water, and 15 square meters rearing area.

Producing the same amount of beef requires 10 kilogram of feed, 22,000 liters of water (including irrigation for feed grains) and 200 square meters of land. Additionally, insects are capable of consuming and converting plant material that is not suitable for human consumption including agricultural waste and associated by-products.

Although some efforts have been made to raise crickets in large numbers (primarily for the fish and pet food trade), these efforts are labor-intensive. Crickets in a confined space with a conventional water supply (usually consisting of open dish-type water feeders) are continuously contaminating their water supply. Crickets typically urinate and defecate in their water supply—which results in bacterial, fungal, or other microbial growth that can kill or detrimentally effect the crickets. Consequently cricket water supplies must be periodically monitored or replaced.

The need exists for an inexpensive and dependable system to continuously supply fresh water to cricket (or other insect) populations in a manner that prevents the crickets from contaminating their water supply. The system described herein comprises a method and system designed to provide water to crickets in a more sanitizing and efficient way—thereby reducing the need for frequently replacing contaminated watering sources. Specifically, a porous and permeable medium is positioned at the bottom of a water reservoir so that as the water (or another selected liquid) moves through the medium, the water moistens the lower exposed surface of the medium. Crickets land on a screen adjacent the medium (so that the crickets are in an inverted position) and drink/absorb the moisture on the surface of the medium.

SUMMARY OF THE INVENTION

This disclosure is directed to a system for providing water to crickets. The system comprises a reservoir container having an aperture in the bottom of the container. A porous and permeable medium positioned over the aperture so that a bottom surface of the medium is exposed to the crickets. In operation, as water fills the container, the water diffuses through the medium and moistens the bottom surface of the medium, thereby allowing the crickets to drink the water from the bottom surface of the medium.

DETAILED DESCRIPTION OF PREFERRED EMBODIMENTS

Figure 1:
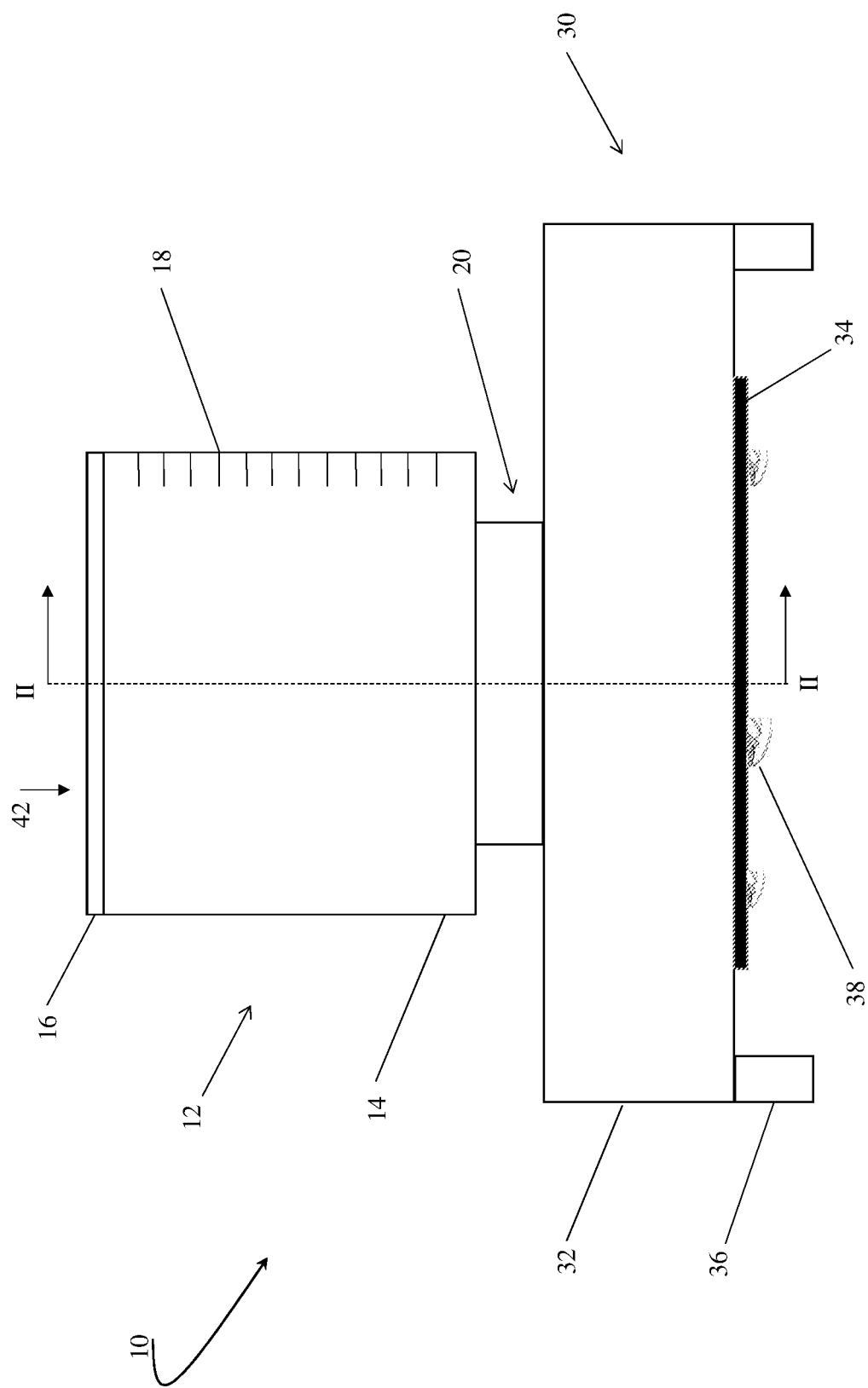
FIG. 1 is a profile view of the cricket watering system described herein, including the section line II.

As generally shown in FIG. 1, the method and apparatus described herein comprises a cricket watering system 10. The watering system 10 generally comprises an upper reservoir assembly 12, a connection device 20, and a lower reservoir assembly 30.

In the preferred embodiment, the upper reservoir assembly 12 comprises a liquid container 14 that is designed to hold water (or a similar liquid). The container 14 has a removable lid 16 so that water can be added to the system 10. The container 14 is generally transparent/translucent and includes volume indicators 18 so that a user can track the amount of water in the system 10. In an alternative embodiment, the container 14 may also comprise a float-type continuous auto-fill mechanism so that when the water in the container 14 gets below a pre-determined volume, a valve (or other mechanical fixture) opens and refills the container 14.

A bottom portion of the container 14 abuts the connection device 20. The connection device 20 connects the container 14 with the lower reservoir assembly 30 and allows liquid to pass freely between the upper reservoir assembly 12 and the lower reservoir assembly 30. The actual connection mechanism(s) between the container 14 and the connection device 20 may comprise any type of connection assembly known in the art—including a screw type connection, a plug type connection, a lockable seal, or any combination thereof—and any other means of creating a water-tight interface. Similarly, the actual connection mechanism(s) between the connection device 20 and the lower reservoir 10 may comprise any type of connection assembly known in the art—including a screw type connection, a plug type connection, a lockable seal, or any combination thereof—and any other means of creating a water-tight interface.

The lower reservoir assembly 30 comprises a hollow housing 32, an insect screen 34, and a plurality of legs 36—which elevate the lower reservoir assembly 30 above the floor of the cricket enclosure. One skilled in the art understands that FIGS. 1 and 2 comprise exemplary embodiments that are not to scale. In an actual deployed system 10, the lower reservoir legs 36 would be an optimal length (probably longer than shown in FIGS. 1 and 2) to facilitate cricket access to the bottom of the housing 32. In the preferred embodiment, crickets 38 land on the insect screen 34 to drink.

Figure 2:
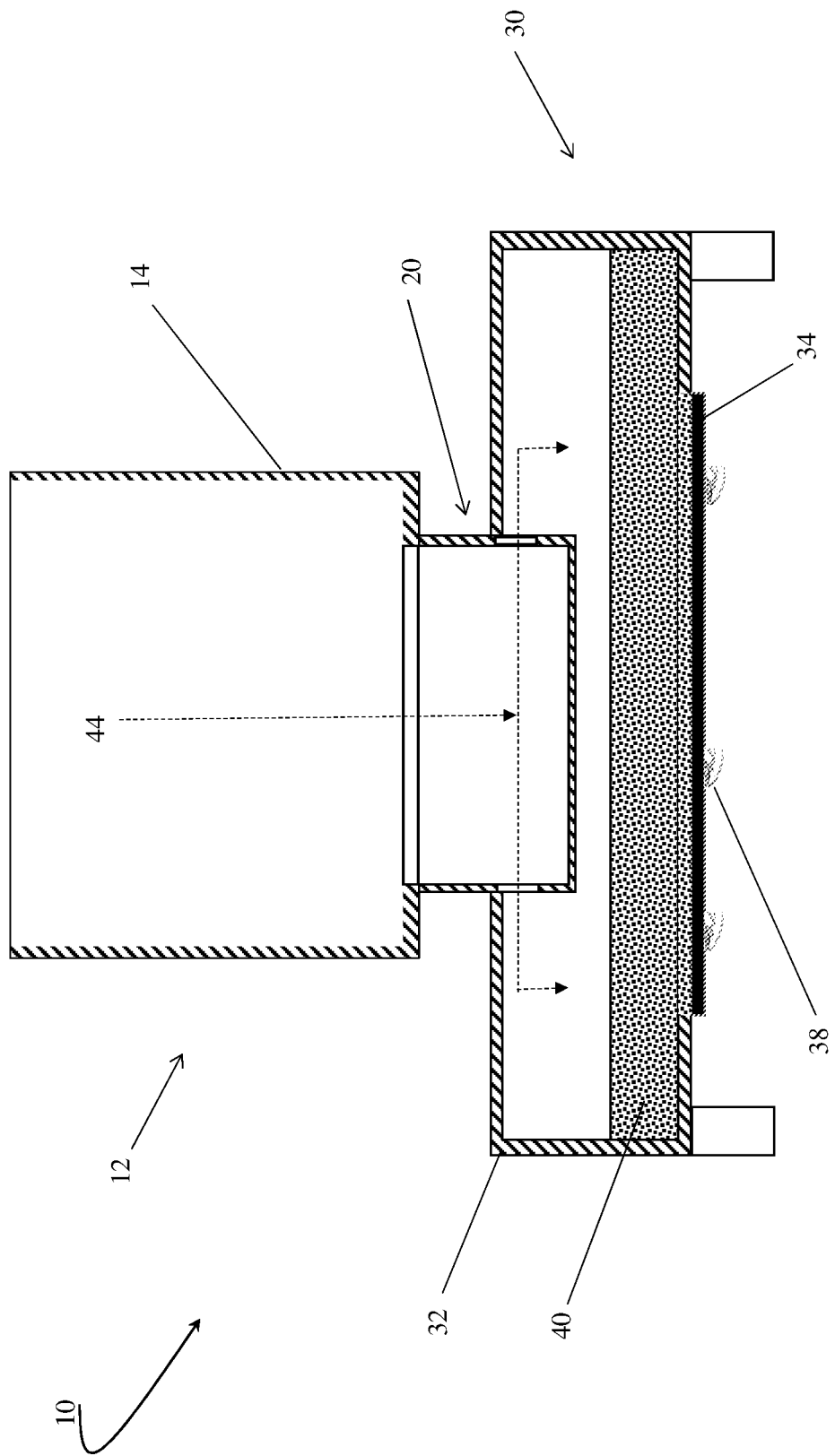
FIG. 2 is a cross sectional view of the cricket watering system along the section line II shown in FIG. 1.

FIG. 2 shows a sectional view of the cricket watering system. As best shown in FIG. 2, the hollow housing 32 holds a porous and permeable medium 40. In the preferred embodiment, the medium 40 comprises polyacrylamide-based crystals. The crystals can be used either alone or in combination with a gel or other materials to enable water to move more or less quickly through the medium 40. Other types of medium may include porous and permeable sandstone, ceramic materials, aggregated natural and manmade materials. The medium may comprises composites of different materials as well as specifically designed plastic membrane configurations, or any other materials that enable to an operator to control the movement of water and/or other fluids through the medium 40. In further alternative embodiments, the liquid may comprise a water (or non-water) based nutrient liquid (for instance, containing essential minerals) that feeds as well as hydrates the crickets.

Note that FIG. 2 shows the medium 40 schematically. In operation, the medium 40 may (or may not) be homogenous. For example, the medium 40 may be layered and may be thicker or thinner than the exemplary embodiment shown in FIG. 2. However, the medium 40 must be configured to allow liquid to diffuse through the medium 40 at a predetermined rate so that relatively dry conditions are maintained with in the cricket enclosure.

In operation, as shown in FIG. 1, a user adds liquid into the liquid container 14 in the upper reservoir assembly 12 in the direction of the arrow 42. The container 14 is transparent/translucent so that the level of the liquid can be monitored by reference to the volume indicators 18. As best shown in FIG. 2, the liquid flows downwardly through the connection device 20 and into the lower reservoir assembly 30 in the direction of the arrows 44 so that the liquid contacts an upper surface of a porous and permeable medium 40. The medium 40 is designed so that the liquid diffuses through the medium 40 at a predetermined rate—resulting in a moistened lower surface of the medium 40. The lower surface of the medium 40 is positioned adjacent an insect screen 34. Crickets 38 position themselves on the insect screen 34 and drink the liquid.

For the foregoing reasons, it is clear that the method and apparatus described herein provides an innovative cricket watering system. The current system may be modified in multiple ways and applied in various applications. For example, although this disclosure references a cricket watering system, the system disclosed herein can also be used to provide water to other living creatures—who should not be considered outside the scope of this disclosure. The disclosed method and apparatus may be modified and customized as required by a specific operation or application, and the individual components may be modified and defined, as required, to achieve the desired result.

Although the materials of construction are not described, they may include a variety of compositions consistent with the function described herein. Such variations are not to be regarded as a departure from the spirit and scope of this disclosure, and all such modifications as would be obvious to one skilled in the art are intended to be included within the scope of the following claims.

The amounts, percentages and ranges disclosed herein are not meant to be limiting, and increments between the recited amounts, percentages and ranges are specifically envisioned as part of the invention. All ranges and parameters disclosed herein are understood to encompass any and all sub-ranges subsumed therein, and every number between the endpoints. For example, a stated range of "1 to 10" should be considered to include any and all sub-ranges between (and inclusive of) the minimum value of 1 and the maximum value of 10 including all integer values and decimal values; that is, all sub-ranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much 10% to a reference quantity, level, value, or amount.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein). The invention illustratively disclosed herein suitably may be practiced in the absence of any element which is not specifically disclosed herein.

What is claimed is:

1. A system for providing liquid to insects to drink, the system comprising:
   a reservoir container having an aperture in a bottom of the container; and
   a porous and permeable medium positioned over the aperture in the bottom of the container so that a bottom surface of the medium is exposed to insects with access to the system, the medium comprising polyacrylamide crystals alone or in combination with gel;
   whereby, as liquid fills the container, the liquid penetrates the medium and moistens the bottom surface of the medium, thereby allowing the insects to drink the liquid.

2. The system of claim 1 wherein the system is structured so that the insects drink in an inverted position.

3. The system of claim 1 wherein the insects comprise crickets.

4. The system of claim 1 further comprising a screen positioned adjacent to the bottom surface of the medium so that the insects land on the screen and drink from the bottom surface of the medium.

5. The system of claim 4 wherein the container comprises upper and lower reservoirs.

6. The system of claim 5 wherein the lower reservoir comprises the medium and the screen.

7. The system of claim 5 further comprising a connection device connecting the upper reservoir and the lower reservoir.

8. The system of claim 5 wherein the upper reservoir has a removable top for adding liquid.

9. The system of claim 5 wherein the upper reservoir is transparent or opaque and includes measurement indicators.

10. The system of claim 1 wherein the liquid comprises water.

11. The system of claim 1 wherein the liquid comprises a nutrient solution.

12. A method of supplying liquid to insects, the method comprising:
   (a) providing a reservoir container having an aperture in a bottom of the container;
   (b) positioning a porous and permeable medium over the aperture so that a bottom surface of the medium is exposed to insects, the medium comprising polyacrylamide crystals alone or in combination with gel;
   (c) pouring liquid into the container so that as the liquid fills the container, the liquid diffuses through the medium and moistens the bottom surface of the medium; and,
   (d) depositing insects adjacent to the container, the container being structured so that the insects assume an inverted position to drink from the bottom surface of the medium.

13. The method of claim 12 wherein the insects comprise crickets.

14. The method of claim 12 wherein the liquid comprises one of water or a nutrient liquid.

15. A system for providing water to crickets, the system comprising:
   a container having an aperture in a bottom of the container;
   a porous and permeable medium covering the aperture in the container so that a bottom surface of the medium is exposed through the aperture, the medium comprising polyacrylamide crystals alone or in combination with gel;
   a liquid at least partially filling the container, the liquid migrating through the medium so that the bottom surface of the medium is wet; and
   crickets in an inverted position, the crickets having access to the bottom surface of the medium so that the inverted crickets drink the liquid on the bottom surface of the medium.

\* \* \* \* \*